United States Patent [19]

Brewer

[11] Patent Number: 4,464,538
[45] Date of Patent: Aug. 7, 1984

[54] METHOD OF SYNTHESIZING DIHYDRO-1,4-DITHIINS

[75] Inventor: Arthur D. Brewer, Puslinch, Canada
[73] Assignee: Uniroyal Ltd., Don Mills, Canada
[21] Appl. No.: 491,009
[22] Filed: May 3, 1983
[30] Foreign Application Priority Data
  May 6, 1982 [CA] Canada ................................ 402400
[51] Int. Cl.[3] ........................................... C07D 335/02
[52] U.S. Cl. ......................................... 549/20; 549/15
[58] Field of Search .................................... 549/15, 20

[56] References Cited
U.S. PATENT DOCUMENTS
  4,319,033 3/1982 Tsai et al. ............................... 549/15

Primary Examiner—Richard Raymond
Attorney, Agent, or Firm—Marvin Bressler

[57] ABSTRACT

Disclosed is a method for synthesizing dihydro-1,4-dithiins by the reaction of an acyloin or a halocarbonyl compound with an organic thiosulfate.

16 Claims, No Drawings

METHOD OF SYNTHESIZING DIHYDRO-1,4-DITHIINS

BACKGROUND OF THE DISCLOSURE

1. Field of the Invention

The present invention is directed to a method for synthesizing dihydro-1,4-dithiins. More specifically, the present invention is directed to a method for forming dihydro-1,4-dithiins by the reaction of an acyloin or a halocarbonyl compound with an organic thiosulfate.

2. Background Of The Prior Art

Compounds of the general class, dihydro-1,4-dithiins have several important uses. U.S. Pat. No. 3,997,323 discloses the use of these dithiins as herbicides. They have also been reported as useful as plant-growth regulants (U.S. Pat. No. 3,920,438.) In U.S. Pat. No. 4,004,018, dihydro-1,4-dithiins compounds are recited to have utility as fungicides and bactericides. A related use, as viricides, is disclosed in U.S. Pat. No. 4,097,580.

The prior art suggests several methods for synthesizing this important class of compounds. One such method is reported in U.S. Pat. No. 4,026,906. The method suggested by the '906 patent comprises the reaction of a halocarbonyl compound with a 1,2-dithiol. A somewhat similar method [Massingill, J. Org. Chem. 35, 823 (1970)] is the reaction of a ketone with a 1,2-dithiol followed by halogenation and ring expansion to a dithiin. A modification of these reactions is disclosed in the above mentioned U.S. Pat. No. 4,026,906, the reaction of the 1,2-dithiol with an alpha-halo-beta-keto-ester. Alternatively, the same '906 patent discloses the reaction of a 1,2-dithiol with a beta-keto-ester followed by ring expansion. In the last two of these syntheses, the first reactive step is followed by decarboxylation. A further method of forming dihydro-1,4-dithiin compounds is disclosed in U.S. Pat. No. 3,755,362. In the '362 patent formation of these dithiins results from the reaction of a mercaptoketone with a thirane. Finally, a still further method of obtaining these important compounds is disclosed in co-pending U.S. patent application, Ser. No. 247,670, filed Mar. 26, 1981, of Tsai et al, now U.S. Pat. No. 4,319,033, in which a dithiol is reacted with acyloin.

Each of the above recited methods of synthesis of dihydro-1,4-dithiin compounds involves the formation and isolation of unpleasant and undesirable intermediates. 1,2-Dithiol compounds, a class of compounds employed in several of the methods mentioned above, have a penetrating, persistent and nauseating odor, even in low concentrations. Mercapto ketones and thiranes are similarly characterized by their vile odor. Furthermore, these compounds are undesirable in that they are chemically unstable and require special handling techniques. Even more important than these esthetically unpleasant characteristics of the reactants employed in the prior art is the fact that expensive apparatus, designed to contain odors, protect workers and abate pollution, is required in all of the above methods for making dihydro-1,4-dithiins.

SUMMARY OF THE INVENTION

A new method has been discovered which overcomes the disadvantages of the prior art methods of synthesizing dihydro-1,4-dithiin compounds. In this method, no reactants are employed which create odor or other handling problems.

In accordance with the instant invention a method is provided for the synthesis of dihydro-1,4 dithiin compounds in which an organic thiosulfate is reacted with an alpha-hydroxyketone (commonly known as an acyloin) or a halocarbonyl compound. The reaction is summarized in Reactions 1 and 2 below.

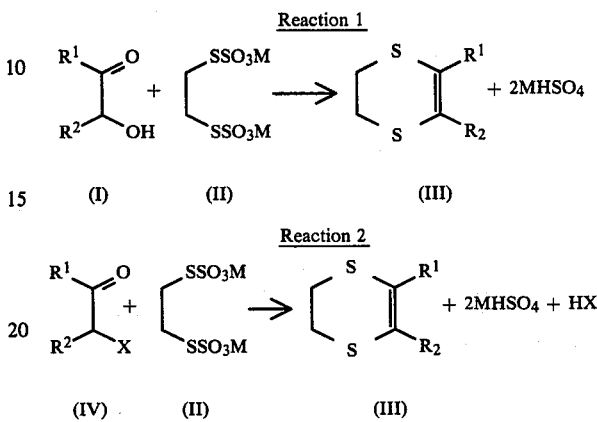

where $R^1$ and $R^2$ are hydrogen or the same or different, aryl groups, alkyl groups have from one to four carbon atoms, or $R^1$ and $R^2$ may be joined to form a chain of 3 to 4 methylene groups; M is a metal atom; and X is a halogen atom.

Reaction 1 is the reaction of an acyloin (I) with an organic thiosulfate ("Bunte Salt") (II) to yield a dihydro-1,4-dithiin (III). In Reaction 2 the organic thiosulfate (II) is reacted with a halocarbonyl compound (IV) to produce a dihydro-1,4-dithiin (III).

DETAILED DESCRIPTION

In the process of the instant invention, the important class of compounds, dihydro-1,4-dithiins, are produced.

Among the 2,3-dihydro-1,4-dithiins that may be synthesized in accordance with the method of this invention are 2,3-dihydro-5-methyl-1,4-dithiin; 2,3-dihydro-5,6-dimethyl-1,4-dithiin; 2,3-diethyl-5,6-dihydro-1,4-dithiin; 2,3-dihydro-5,6-dipropyl-1,4-dithiin; 2,3-dibutyl-5,6-dihydro-1,4-dithiin; 2,3-dihydro-5,6-di(2-methylpropyl)-1,4-dithiin; and 5,6,7,8-tetrahydro-1,4-benzodithiin.

The process of the instant invention includes the reaction of an alpha-hydroxyketone (acyloin) of the formula $R^1COCHOHR^2$, where $R^1$ and $R^2$ are selected from hydrogen, the same or different alkyl group having from 1 to 4 carbon atoms or aryl groups, or $R^1$ and $R^2$ may be joined together to form a chain of 3 or 4 methylene groups, with an organic thiosulfate having the formula $(H_2CSSO_3M)_2$ (II), where M is a metal atom. This thiosulfate class of compounds are known as "Bunte Salts" [See Bunte, Ber. 7, 646 (1874)]. It is preferred that the metal atom be an alkali metal. Although any alkali metal may be used in the organic thiosulfate reactant of this invention, sodium and potassium are particularly preferred. Of the organic thiosulfates within the contemplation of this reactant, sodium ethylene thiosulfate is particularly preferred.

In another preferred embodiment of this invention, the alpha-hydroxyketone (acyloin) is replaced with a halocarbonyl compound having the formula, $R^1COCHXR^2$(IV), where $R^1$ and $R^2$ have the same definition as given for the acyloin, and where X is a halogen atom. Any halogen atom may be employed in the halocarbonyl compound of this invention. However, of the halogens, chlorine or bromine are preferred. The halocarbonyl compound is reacted with the organic thiosulfate as described above.

The two basic reactions within the contemplation of the method of this invention are as follows:

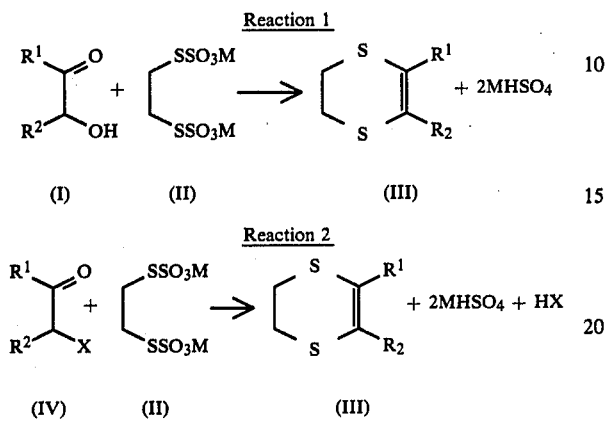

The dihydro-1,4-dithiin product of each of these reactions (compound III) includes substituents $R^1$ and $R^2$, which are hydrogen or the same or different alkyl groups having from 1 to 4 carbon atoms, aryl groups or are joined together to form a chain of 3 or 4 methylene groups.

In a alternate embodiment of this invention, a catalyst, specifically a phase-transfer catalyst, is employed to catalyze the process of this invention. The class of catalysts preferred to catalyze the reaction of the alpha-hydroxyketone or alpha-halocarbonyl compound with the organic thiorsulfate is a tetraalkyl ammonium halide.

The following examples are provided to illustrate the scope of the invention. They should, therefore, not be construed as limiting the invention in any way such as by limiting the invention to these examples.

EXAMPLE 1

Ten grams of sodium ethylene thiosulfate, prepared in accordance with the procedure given by Magidson and Krol, Trans. Sci. Chem. Pharm. Inst. (Moscow) 6, 21 (1923), (CA 22, 4077) was added to 100 ml water made acid by the addition of 8 ml hydrochloric acid. To this was added 2.95 grams of acetoin. This reaction mixture was gently refluxed with stirring. After two hours a pale yellow oil was observed floating on the surface. The reaction mixture was cooled and extracted with methylene chloride. The extracts were reduced in volume, yielding a pale yellow oil which was substantially 2,3-dihydro-5,6-dimethyl-1,4-dithiin. 3.4 grams of the oil was recovered (theoretical yield: 4.89 grams). The nuclear magnetic resonance (NMR) (CDCl$_3$) 1.865 (singlet, integral 3); 3.12 delta (singlet, integral 2).

EXAMPLE 2

Example 1 was repeated, except that acetoin was replaced with phenacyl bromide (6.7 grams). In addition, 0.25 gram tetrabutyl ammonium bromide was added as a catalyst. The reaction was conducted as in Example 1 to yield 5.4 grams of an oil which was substantially 2,3-dihydro-5-phenyl-1,4-dithiin. NMR (CDCl$_3$) 3.20 delta (complex singlet), 6.28 delta (singlet), 7.15–7.5 delta multiplet).

EXAMPLE 3

Example 1 was repeated except that, instead of 10 grams of sodium ethylene thiosulfate, 14.5 grams of the thiosulfate was reacted, in accordance with the procedure of Example 1, with 5.2 grams of 3-chloro-2-butanone. A pale yellow oil was obtained, substantially all 2,3-dihydro-5,6-dimethyl-1,4-dithiin. NMR (CDCl$_3$) 1.86 delta, 3.12 delta, along with some impurities.

EXAMPLE 4

The method of Example 1 was repeated employing 12.85 grams of sodium methylene thiosulfate which was reacted with 3.8 grams propioin, also known as 4-hydroxy-hexan-3-one. This yielded a greenish oil which was substantially all 2,3-diethyl-5,6-dihydro-1,4-dithiin. NMR (CDCl$_3$) 1.128 (triplex, integral 3), 2.22 at delta (quartet, integral 2), 3.07 delta, (singlet, integral 2).

The above preferred embodiments and examples are given for illustrative purposes only. They should not, in any way, be deemed to limit or restrict the invention to the preferred embodiment and examples given herein. These embodiments and examples will suggest, to those skilled in the art, other embodiments and examples within the scope and spirit of the instant invention. Therefore, the scope of the invention should be limited only by the appended claims.

What is claimed is:

1. A method for making a dihydro-1,4-dithiin having the formula

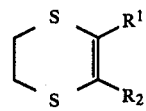

where $R^1$ and $R^2$ are hydrogen; the same or different aryl groups; alkyl having one to four carbon atoms; or $R^1$ and $R^2$ are joined to form a chain of 3 to 4 methylene groups by the reaction of an organic thiosulfate having the formula,

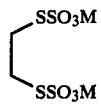

where M is a metal ion, with an acyloin having the formula

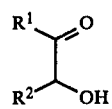

where $R^1$ and $R^2$ are as defined above.

2. A method in accordance with claim 1 wherein a phase-transfer catalyst is added to catalyze the reaction of said thiosulfate and said acyloin.

3. A method in accordance with claim 2 wherein said catalyst is a tetraalkyl ammonium halide.

4. A method for making a dihydro-1,4-dithiin having the formula

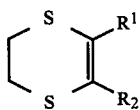

where $R^1$ and $R^2$ are hydrogen; the same or different aryl group, alkyl having one to four carbon atoms; or $R^1$ and $R^2$ are joined to form a chain of 3 to 4 methylene groups by the reaction of an organic thiosulfate having the formula,

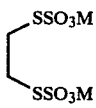

where M is a metal ion, with a halocarbonyl compound, having the formula

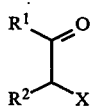

where $R^1$ and $R^2$ are defined as above and X is a halogen atom.

5. A method in accordance with claim 4 wherein a phase-transfer catalyst is added to catalyze the reaction of said thiosulfate and said halocarbonyl compound.

6. A method in accordance with claim 5 wherein said catalyst is a tetraalkyl ammonium halide.

7. A method in accordance with claim 1 wherein said metal atom is an alkali metal atom.

8. A method in accordance with claim 4 wherein said metal atom is an alkali metal atom.

9. A method in accordance with claim 7 wherein said alkali metal atom is selected from the group consisting of sodium and potassium.

10. A method in accordance with claim 8 wherein said alkali metal atom is selected from the group consisting of sodium and potassium.

11. A method in accordance with claim 4 wherein said halogen atom is selected from the group consisting of chlorine and bromine.

12. A method in accordance with claim 1 wherein said acyloin is acetoin (3-hydroxybutan-2-one) and said dithiin synthesized is 2,3-dihydro-5,6-dimethyl-1,4-dithiin.

13. A method in accordance with claim 1 wherein said acyloin is propioin (4-hydroxyhexan-3-one) and said dithiin synthesized is 2,3-diethyl-5,6-dihydro-1,4-dithiin.

14. A method in accordance with claim 4 wherein said halocarbonyl compound is a phenacyl halide and said dithiin synthesized is 2,3-dihydro-5-phenyl-1,4-dithiin.

15. A method in accordance with claim 13 wherein said phenacyl halide is phenacyl bromide.

16. A method in accordance with claim 4 wherein said halocarbonyl compound is 3-chloro-2-butanone and said dithiin synthesized is 2,3-dihydro-5,6-dimethyl-1,4-dithiin.

* * * * *